United States Patent [19]

Kern et al.

[11] 4,149,255

[45] Apr. 10, 1979

[54] METHOD AND ARRANGEMENT FOR THE AUTOMATIC OBSERVATION OF INTERFACIAL PHENOMENA

[75] Inventors: Winfried Kern; Wilhelm Valentin, both of Erftstadt, Fed. Rep. of Germany

[73] Assignee: Hoechst Aktiengesellschaft, Frankfurt am Main, Fed. Rep. of Germany

[21] Appl. No.: 793,762

[22] Filed: May 4, 1977

[30] Foreign Application Priority Data

May 7, 1976 [DE] Fed. Rep. of Germany ....... 2620137

[51] Int. Cl.² .................. G01N 25/12; G01F 11/00
[52] U.S. Cl. ........................................ 364/524; 73/19
[58] Field of Search ............... 235/151.12, 151.13, 235/151.3; 73/19; 364/524, 555

[56] References Cited

U.S. PATENT DOCUMENTS

| | | | |
|---|---|---|---|
| 3,740,320 | 6/1973 | Arthur | 73/19 |
| 3,949,590 | 4/1976 | Boillot | 73/19 |
| 3,964,864 | 6/1976 | Dahms | 73/19 |

FOREIGN PATENT DOCUMENTS 1623097  5/1971  Fed. Rep. of Germany.

OTHER PUBLICATIONS

Smith: Use of Thermodesorption Technique for Studying Gas Adsorption, Journal of Colloid and Interface Science, vol. 34, No. 3, pp. 401–405 Nov. 1970.

Primary Examiner—Felix D. Gruber
Attorney, Agent, or Firm—Connolly and Hutz

[57] ABSTRACT

Interfacial phenomena are observed employing an electronically compensated vacuum micro-balance for weighing the specimen mixture under observation. The gas pressure in the vacuum micro-balance is determined by means of a buoyancy element. During the weighing operation the weights of the specimen and of the buoyancy element and also the temperature of the specimen are determined at intervals of 0.1 to 60 seconds. The measured values thus obtained are supplied to converters whereby they are converted into initial values which are computer-readable. The measured values thus converted are stored intermediately in a computer, successive values being compared with one another until 2 to 50 successive values of the weight of the specimen differ from one another by less than $50\gamma$ $1\gamma$ means $10^{-6}$g. The result of this latter specimen weight comparison, together with the values of the gas pressure and of the temperature, is printed out by a printer connected to the computer. Thereafter the above-mentioned observations are repeated, in accordance with a program stored in the said computer for the control and monitoring of the observations in conformity with predetermined instructions and conditions.

2 Claims, 2 Drawing Figures

METHOD AND ARRANGEMENT FOR THE AUTOMATIC OBSERVATION OF INTERFACIAL PHENOMENA

The present invention relates to a method and arrangement for the automatic observation of interfacial phenomena, more specifically of sorption phenomena, employing a first highly sensitive electronically compensated vacuum micro-balance for weighing the specimen, under observation, a second highly sensitive electronically compensated vacuum micro-balance having a gas connection to the first vacuum micro-balance for measuring the gas pressure therein by means of a buoyancy element, and a vapour pressure thermometer for measuring the temperature.

The observation of adsorption and desorption phenomena is an requirement, e.g. in all those cases in which it is desirable to determine the specific BET-surfaces or pore volumes and distribution of pore radii, or to investigate drying phenomena. All analyses which are based on the observation of sorption phenomena are expensive in respect of time. For example 12 to 16 hours are needed for the determination of the pore volume of a catalyst, e.g. for the recording of an adsorption isotherm, and a further 8 hour period is needed for the recording of the desorption isotherm which is performed immediately after the recording of the adsorption isotherm.

For this reason various attempts have already been made to develop automatically-operating vacuum microbalances.

BACKGROUND OF THE INVENTION

The recording of a nitrogen adsorption isotherm employing a known automatically-operating vacuum microbalance is effected by registering the values of the variation in the weight of the specimen under observation with a multi-channel compensation recorder. Different gas pressures in the vacuum micro-balance are then controlled through a manostat by a buoyancy manometer which permits various pressure stages to be adjusted according to a preselected programme. Pressure regulation is effected by means of a minor quantity of gas which is kept constant and admitted to the vacuum micro-balance. Once the desirable nominal pressure value is attained, the gas admitted to the vacuum micro-balance is partially removed by means of a pump until the preselected gas pressure remains constant.

This procedure has serious disadvantages in respect of the following points:

1. Preliminary tests are necessary in order to ascertain how much time is required for adjustment of the equilibrium. Depending upon the specimen used and the gas pressure, between 5 and 200 minutes are needed for adjustment of the equilibrium.

2. A certain safety margin for the time must be allowed in order to be sure that the equilibrium has adjusted.

3. The statement of the variation in weight of the specimen is made in the form of a graph from which the actual weight difference must be laboriously interpolated.

4. For large variations in weight of the specimen, the hundreds and thousands decades must be laboriously deduced from the record strip, because the decade is stepped up or stepped down automatically when the recorder carriage strikes the limit points. The relevant hundreds or thousands decade has to be reconstructed from the number of jumps.

5. The pressure indication can also only be obtained inaccurately, because only the width of the recorder is available for the entire range of pressure.

6. The association of the variation in weight with the corresponding gas pressure is likewise a time-consuming operation.

7. The pressure regulation is effected by a regulated exhaustion of inflowing gas. Due to the slight pressure variations which then occur, the highly sensitive vacuum micro-balance is set into oscillations which lead to inaccuracy in detecting the equilibrium state.

SUMMARY OF THE INVENTION

It is therefore an object of the present invention to provide a method of observing interfacial and more specifically sorption phenomena employing a first highly sensitive electronically compensated vacuum micro-balance for weighing the specimen under observation, and a second highly sensitive electronically compensated vacuum micro-balance having a gas connection to the first vacuum micro-balance for measuring the gas pressure therein by means of a buoyancy element. The weights of the specimen and of the buoyancy element and also the temperature of the specimens are determined at intervals of 0.1 to 60 seconds, preferably 5 to 10 seconds; the measured values thus obtained are supplied to converters which are computer-readable; the measured values thus converted are stored intermediately in a computer, successive values being compared with one another until 2 to 50, preferably 5 to 10, successive values of the weight of the specimen differ from one another by less than $50\gamma$, preferably by less than $1\gamma$; the result of this latter specimen weight comparison, together with the values of the gas pressure and of the temperature, being printed out by a printer connected to the said computer; and thereafter the above-mentioned observations are repeated, in accordance with a programme stored in the said computer for the control and monitoring of the observations in conformity with predetermined instructions and conditions.

BRIEF DESCRIPTION OF THE DRAWINGS

Novel features and advantages of the present invention will become apparent to one skilled in the art from a reading of the following detailed description in conjunction with the accompanying drawings wherein similar reference characters refer to similar parts and in which.

DESCRIPTION OF THE PREFERRED EMBODIMENTS

Figure 1:
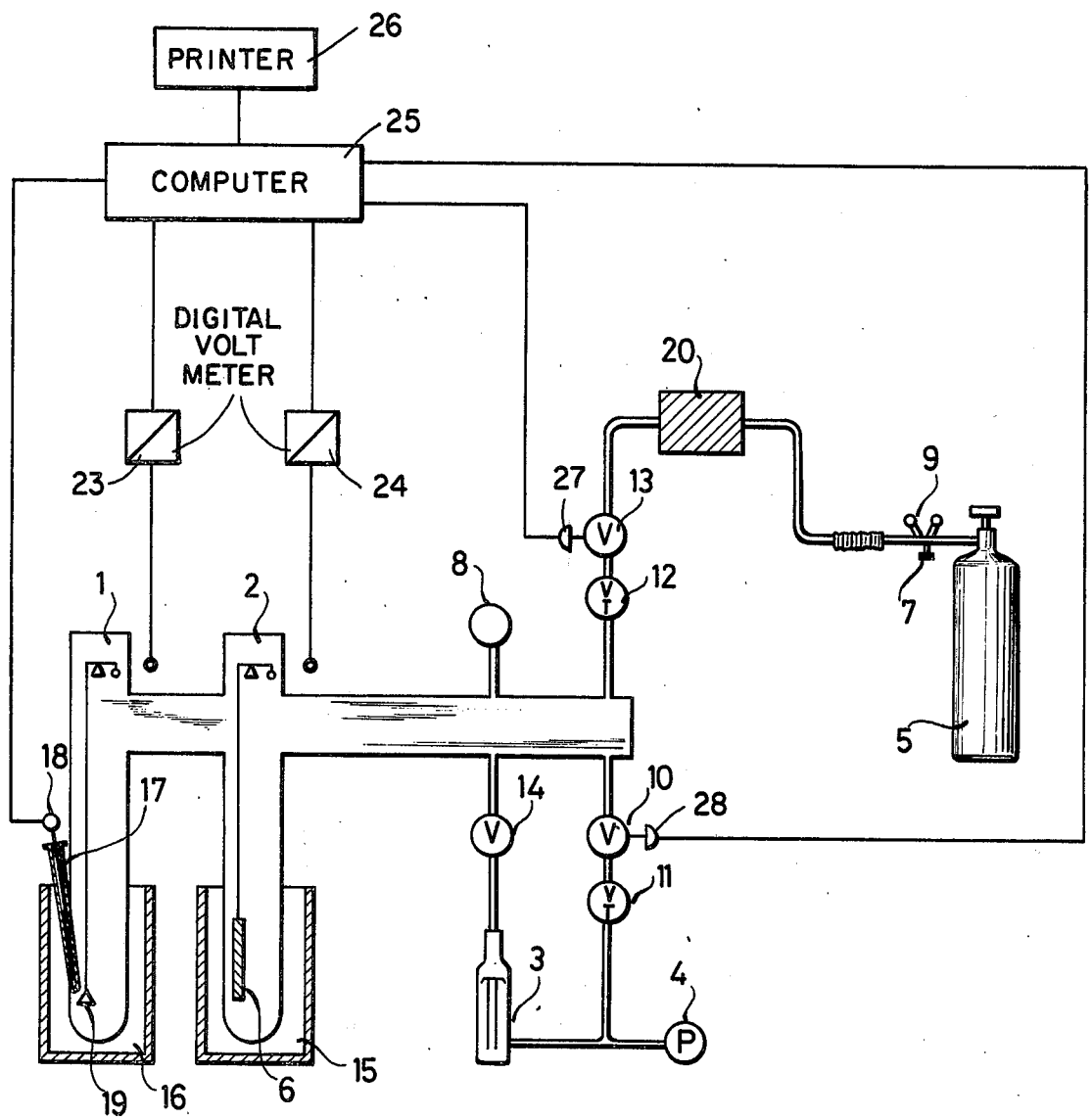
FIG. 1 is a schematic diagram showing apparatus for performing the process of the invention.
Figure 2:
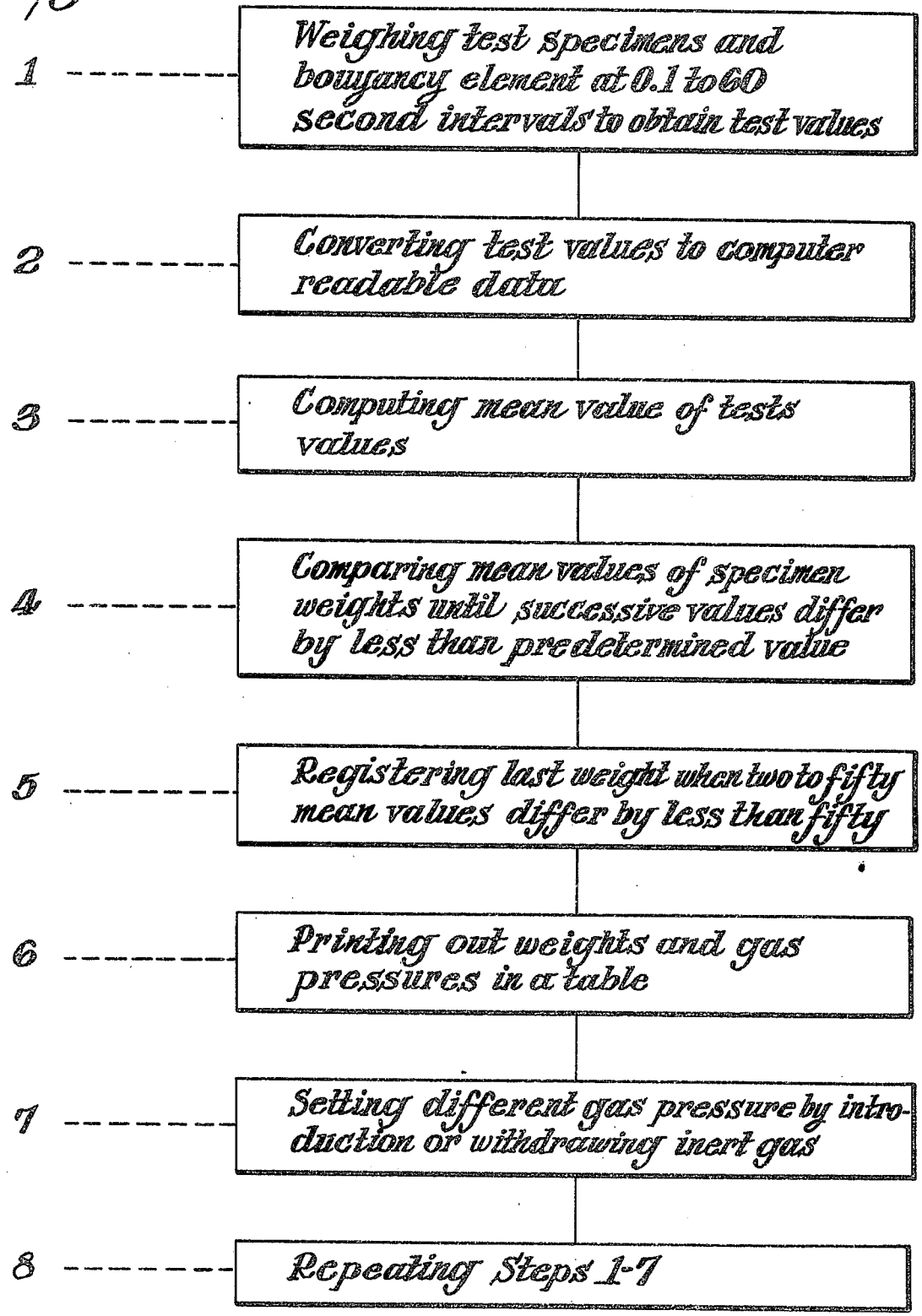
FIG. 2 is a flow sheet showing the steps of the invention.

The process of the present invention is advantageously carried out employing an arrangement in which: the gas pressure in the vacuum micro-balances 1,2 is adjusted by the computer in a first step, the second vacuum micro-balance 2 being brought out of equilibrium by reference to a scaled-down predetermined electronically compensated tare weight; and in a second step the disequilibrium of the second vacuum micro-balance 2 closes an electric contact which effects the opening of a solenoid valve 13, whereby gas is permitted to flow from a gas cylinder 5 into the vacuum micro-balances 1,2 until equilibrium is attained by the second vacuum micro-balance 2; the said electric contact controlling the solenoid valve 13 being opened when equilibrium is attained by the second vacuum micro-balance 2 and the solenoid valve 13 thereupon being closed by spring force.

A first advantage of the arrangement described resides in the fact that a manually actuated throttle valve 12 is interposed between the vacuum micro-balances 1, 2 and the solenoid valve 13, and that the vacuum micro-balances 1,2 are degassed through a solenoid valve 10 by means of a vacuum pump 4 and that the degassed vacuum micro-balances 1, 2 are evacuated through the open manual valve 14 down to $10^{-6}$ mm Hg by means of a diffusion pump 3 when the solenoid valve 10 is closed.

A second advantage resides in the fact that a manually actuated throttle valve 11 is interposed between the vacuum pump 4 and the solenoid valve 10.

A third advantage resides in the fact that the temperature of the vacuum micro-balance 2 is adjustable to 20° C. by means of a thermo-regulator 15 and the temperature of the specimen 19 is adjusted by means of a thermo-regulator 16, the specimen temperature being preferably adjusted, in the event of low temperature measurements, by means of a thermo-regulator 16 incorporating a Dewar vessel, in which liquid nitrogen is evaporated.

For the observation at interfaces at increased temperatures, the invention provides for an electrically heatable furnace to be used as thermo-regulator 16, and for the electrically heatable furnace to be regulated by reference to a thermometer 18, which may preferably be a vapour pressure thermometer.

A further preferred feature provides for a uniform tare weight to be adopted for the specimen under given experimental conditions and for the uniform tare weight to be comparable with the specific gravity of the specimen.

The arrangement of the present invention for the automatic observation of interfacial, more specifically of sorption phenomena, will now be further described with reference to the accompanying diagrammatic drawing FIG. 1.

Specimen 19 is weighed by means of the vacuum microbalance 1. The arrangement is degassed by means of the vacuum pump 4 with the valves 10, 11, 12, 14 open and with the valve 13 closed. As soon as a pressure of $10^{-2}$ mm Hg has been attained, the arrangement is evacuated down to $10^{-6}$ mm Hg by means of the diffusion pump 3 with the valve 10 closed, whereupon the valve 14 is closed. The pressure is determined by the buoyancy element 6 associated with the vacuum micro-balance 2 and can be controlled by the manometer 8. A temperature of 20° C. is adjusted in the vacuum micro-balance 2 by means of the thermo-regulator 15. The temperature in vacuum micro-balance 1 is controlled by means of a thermo-regulator 16, incorporating a Dewar vessel for low temperature measurements or by means of an electrically heatable furnace for high temperature measurements. In this latter case the furnace is regulated by reference to the thermometer 18. The thermometer 18 located in the temperature pocket 17 terminating in the vicinity of specimen 19. The gas pressure to be adjusted is preselected by the computer 25 and communicated to the vacuum micro-balance 2 in the form of a tare variation. The disequilibrium in the vacuum micro-balance 2 causes an electric contact 27 to be closed, whereby the solenoid valve 13 is opened. Test gas then flows from the compressed gas cylinder 5 after passing through a cleaning stage 20 into the arrangement until the vacuum micro-balance 2 has once more reached the equilibrium state due to the now greater buoyancy of the float element 6. This causes the electric contact 27 for the valve 13 to be reopened and the valve 13 to be closed. The variation in weight of the specimen 18 is stored and compared by the computer 25. After the equilibrium state of the specimen 19 is attained, which is the case as soon as the weight of the specimen 19 ceases to vary, the weight of the specimen 19 together with the gas pressure values and temperature values are printed out by printout 26. Next, the computer 25 causes further measurements to be made in accordance with the programme stored. As soon as the gas pressure is at the highest preselected value, the computer 25 switches-over and causes stagewise falling gas pressure values to be measured. The vacuum micro-balance put into the disequilibrium state by the computer 25 causes a second electric contact 28 to be actuated keeping the valve 10 open until the equilibrium state of the vacuum micro-balance 2 has been attained again.

After the lowest preprogrammed value has been measured with falling gas pressure stages and printed out at 26, the computer 25 automatically causes the apparatus arrangement to be switched off.

The arrangement according to the invention will now be described in more detail with reference to a nitrogen sorption analysis.

74.6 mg of $\gamma$-$MnO_2$ consisting of particles with a size of 30 to 60$\mu$ was weighed-in on the vacuum micro-balance 1. A mixture of quartz chips and gold wire was used as tare, the mixing ratio being selected in accordance with the density of the specimen. The residual buoyancy was measured in pure nitrogen at various pressures and was already taken into consideration by the computer 25 when printing out the weight values. The tar weight which compensates the weight of the specimen 19 is shown diagrammatically as a circle at the right hand side of the balance beam. The tare weight must have a specific gravity identical with that of the specimen. Gold and quartz are used in a mixing ratio which is determined in accordance with the following formula $$\text{quartz proportions in weight \%} = \frac{(d_{specimen} - d_{gold}) \cdot d_{quartz}}{(d_{quartz} - d_{gold}) \cdot d_{specimen}} \cdot 100$$

$$\text{gold proportions in weight \%} = \frac{(d_{quartz} - d_{specimen}) d_{gold}}{(d_{quartz} - d_{gold}) \cdot d_{specimen}}$$

d = density

Next, the vacuum pump 4 and the diffusion pump 3 were used for evacuation ($10^{-6}$ mm Hg) and the specimen was heated to 70° C. to constant weight. The specimen underwent a loss in weight of 1.87 mg. After cooling, the Dewar vessel 16 was filled with liquid nitrogen and the test programme was fed into the computer 25. Into the computer are then fed the conditions under which the metering should occur. These were the following in the specific example:

1. The nominal pressure values to be established, in mm Hg:

50, 100, 150, 200, 242, 271, 324, 374, 443, 493, 531, 559, 581, 599, 653, 680, 705, 719, 733, 744, 750.

2. The maximum pressure of 750 mm Hg, above which to determine the desorption isotherm.
3. The factor for the conversion of the weight of the buoyancy element 6 into the corresponding gas pressure (in the specific case 1000$\gamma$ weight variation corresponded to a pressure variation of 8.55 mm Hg).
4. The printing out of the last mean value of 6 equilibrium measurements to be effected when the average of the 6 weight values read differs from an average value of likewise 6 weight values previously determined by the computer by less than 0.5$\gamma$. For this purpose weight values of the specimen should be received in the computer at intervals of 5 seconds.
5. The entire arrangement to be switched off after the printing out of the desorption value at 50 mm Hg.

After feeding in these conditions, the computer 25 is started. The initial weight of the specimen is first determined under high vacuum at the temperature of liquid nitrogen.

The weight values of the specimen and the pressure values recorded at intervals of 5 seconds are supplied to the converters, which may be digital volt meters 23 and 24, communicated to the computer 25, stored therein and mean values are formed. As soon as 2 mean values each of 6 weights differ by less than 0.5$\gamma$, the last average value is printed out together with the associated gas pressure mean value. The measured temperature is not printed out separately, because the measurement takes place at the temperature of boiling nitrogen. The computer stops at this point. In order to start the actual test series, the value 14 is closed manually and the diffusion pump 3 is switched off. After allowing for the zero point of the vacuum micro-balance 2 by feeding in a correction magnitude into the computer, the computer is started again for fully automatic observation of interfacial phenomena.

The computer first modifies the tare weight of the buoyancy element 6 of the vacuum micro-balance 2 which is brought out of equilibrium. This causes an electric contact 27 to be closed and the solenoid valve 13 to be opened. Next, gas from the gas cylinder 5 is first passed through the drying device 20, and then gradually admitted, through the throttle valve 12, to the vacuum micro-balance 2, wherein the element 6 undergoes more buoyancy which causes the state of equilibrium to be restored. This causes the electric contact 27 to be opened and the solenoid valve 13 to be closed.

After this programmed pressure increase, the computer receives the specimen weight and the gas pressure values at intervals of 5 seconds, processes these values as described and causes the printer to print out the weight and pressure value in the event of two mean values each of 6 weights of the specimen differing from one another by not more than 0.5$\gamma$.

This process is repeated until the maximum pressure of 750 mm Hg fed in is exceeded. From this point onwards the tare weight of the buoyancy element 6 is increased according to the test programme and programme fed in. This causes the vacuum micro-balance 2 to be set into a state of disequilibrium, whereby a second electric contact 28 is closed and the valve 10 leading to the vacuum pump 4 is opened. Gas is exhausted whereby the state of equilibrium is restored in the vacuum micro-balance 2. As a result the second electric contact 28 is opened again, which in turn closes the valve 10. The computer again receives the weight of the specimen and the gas pressure value at intervals of 5 seconds, processes these values as described and again causes the printer 26 to print out the weight and pressure value in the event of 2 mean values, each of 6 weights of the specimen, differing from one another by not more than 0.5$\gamma$.

This operation is repeated until the pressure falls below the minimum value of 50 mm Hg fed in whereupon the computer causes the arrangement to be switched off.

The test results are indicated in the following table.

TABLE

| Adsorption and desorption isotherms of $\gamma-MnO_2$ at $-196°$ C. Initial weight of heated specimen : 72.73 mg | | | |
|---|---|---|---|
| Relative weight (mg) | Corrected weight increase (mg) | Pressure P (mm Hg) | Pressure ratio P/Po |
| 4.0487 | 0 | 0 | 0 |
| 5.2140 | 1.1619 | 52.3 | 0.0690 |
| 5.3614 | 1.3058 | 103.6 | 0.1367 |
| 5.4869 | 1.4287 | 154.9 | 0.2044 |
| 5.5804 | 1.5191 | 197.6 | 0.2607 |
| 5.6702 | 1.6066 | 240.2 | 0.3169 |
| 5.7384 | 1.6725 | 274.3 | 0.3619 |
| 5.8342 | 1.7655 | 325.4 | 0.4293 |
| 5.9323 | 1.8604 | 376.8 | 0.4971 |
| 6.0554 | 1.9793 | 444.5 | 0.5864 |
| 6.1578 | 2.0792 | 496.5 | 0.6550 |
| 6.2401 | 2.1592 | 530.6 | 0.7000 |
| 6.3080 | 2.2256 | 556.3 | 0.7339 |
| 6.3840 | 2.3001 | 581.8 | 0.7675 |
| 6.4342 | 2.3491 | 598.4 | 0.7894 |
| 6.6514 | 2.5630 | 650.2 | 0.8578 |
| 6.8335 | 2.7440 | 684.0 | 0.9024 |
| 6.9454 | 2.8539 | 701.4 | 0.9253 |
| 7.0741 | 2.9819 | 718.4 | 0.9476 |
| 7.2437 | 3.1509 | 735.8 | 0.9707 |
| .3445 | 3.2514 | 743.7 | 0.9811 |
| 7.5457 | 3.4519 | 751.6 | 0.9916 |
| 7.5463 | 3.4519 | 751.7 | 0.9917 |
| 7.4591 | 3.3652 | 747.4 | 0.9860 |
| 7.3769 | 3.2837 | 739.1 | 0.9751 |
| 7.2243 | 3.1317 | 722.1 | 0.9526 |
| 7.1026 | 3.0117 | 704.9 | 0.9300 |
| 7.0030 | 2.9127 | 687.9 | 0.9075 |
| 6.8515 | 2.7638 | 653.8 | 0.8625 |
| 6.6807 | 2.5959 | 602.2* | 0.7945 |
| 6.6351 | 2.5509 | 585.1 | 0.7719 |
| 6.5762 | 2.4935 | 559.2 | 0.7377 |
| 6.5257 | 2.4450 | 533.8 | 0.7042 |
| 6.4670 | 2.3880 | 499.9 | 0.6595 |
| 6.3914 | 2.3151 | 448.3 | 0.5914 |
| 6.1281 | 2.0563 | 379.2** | 0.5003 |
| 5.8595 | 1.7913 | 328.3 | 0.4331 |
| 5.7472 | 1.6814 | 277.2 | 0.3657 |
| 5.6784 | 1.6144 | 243.0 | 0.3206 |
| 5.5716 | 1.5115 | 191.8 | 0.2530 |
| 5.4971 | 1.4385 | 157.7 | 0.2080 |
| 5.3749 | 1.3196 | 106.5 | 0.1405 |
| 5.2547 | 1.2027 | 55.2 | 0.0728 |
| 5.1503 | 1.0987 | 38.4 | 0.0507 |

Po = N$_2$ saturation pressure at $-196°$ C.
*Equilibrium adjustment 5 minutes
**Equilibrium adjustment 80 minutes.

We claim:

1. A method for automatic detecting of isotherms in sensitive electronically compensated vacuum-microbalance comprising the steps of:
   determining the weight of the specimen after time intervals of 0.1 to 60 seconds;
   determining the gas pressure in the vacuum-microbalance at said same time intervals;
   feeding the test values of the weight of the specimen and gas pressure by means of a converter into a computer;

forming the mean value of individual test values of the specimen weights and gas pressure in the computer;

comparing the individual mean values of the specimen weights in the computer until successive values differ from one another by less than a predetermined value;

communicating and noting the mean value of the last weight of the specimen as soon as 2 to 50 mean values of the specimen weights differ from one another by less than 50; and registering the specimen weight and gas pressure in the vacuum-microbalance by printing them out in a table.

2. The method of claim 1, wherein after printing out the mean value of the last specimen weights in the sensitive electronically compensated vacuum-micro-balance for a preselected gas pressure, a different preselected gas pressure is set therein by the introduction of or withdrawal of inert gas and the method as set forth in claim 1 is repeated.

* * * * *